US00PP09389P

United States Patent [19]

Winchel

[11] Patent Number: Plant 9,389

[45] Date of Patent: Dec. 5, 1995

[54] HYBRID TEA ROSE PLANT NAMED 'WEKJOE'

[75] Inventor: Joseph Winchel, Harbor City, Calif.

[73] Assignee: Weeks Wholesale Rose Grower, Inc., Upland, Calif.

[21] Appl. No.: 342,446

[22] Filed: Nov. 18, 1994

[51] Int. Cl.[6] ..... A01H 5/00

[52] U.S. Cl. ..... Plt./11

[58] Field of Search ..... Plt./11, 12

[56] References Cited

U.S. PATENT DOCUMENTS

| | | | |
|---|---|---|---|
| P.P. 5,067 | 7/1983 | Meilland | Plt./11 |
| P.P. 6,861 | 6/1989 | Christensen | Plt./11 |
| P.P. 7,826 | 3/1992 | Winchel | Plt./11 |

*Primary Examiner*—Howard J. Locker

*Attorney, Agent, or Firm*—Christie, Parker & Hale

[57] ABSTRACT

A new variety of Hybrid Tea rose suitable for garden decoration, having flowers of white coloration edged with pink.

1 Drawing Sheet

BACKGROUND OF THE INVENTION

This invention relates to a new and distinct variety of Hybrid Tea rose. The varietal denomination of the new variety is 'Wekjoe'. The plant is a bushy upright seedling cultivated for outdoor garden decoration. It has as its seed parent the variety known as 'Gold Medal' (U.S. Plant Pat. No. 5,177') and its pollen parent is unknown.

SUMMARY OF THE INVENTION

Among the features which distinguish the new variety from other presently available and known commercial rose cultivars are the following combination of characteristics: its extremely large foliage carried to the ground, its very vigorous, bushy, tall, upright habit, its cream colored flowers edged with bright pink, and its extremely long stems. 'Wekjoe' may be asexually propagated by cuttings, budding, and grafting.

Asexual reproduction of the new variety as performed in Kern County and Upland, Calif., by budding shows that the foregoing and other distinguishing characteristics come true to form and are established and transmitted through succeeding propagations.

COMPARISON WITH PARENT

The new rose may be distinguished from its seed parent, 'Gold Medal' by the following combination of characteristics: whereas the new variety has flowers of cream edged with pink, 'Gold Medal' has flowers of deep gold coloration. The seed parent has medium large leaves and leaflets, whereas 'Wekjoe' has significantly larger foliage. 'Wekjoe' is classified as a Hybrid Tea bearing mostly one flower per stem, whereas 'Gold Medal' is classified as a Grandiflora bearing mostly clusters of flowers.

The pollen parent of the new variety is unknown.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of August. Phenotypic expression may vary with environmental, cultural and climatic conditions, as well as differences in conditions of light and soil.

FLOWER

The new variety bears its flowers usually singly, sometimes two to three per stem. Flowers are borne in regular flat to rounded clusters on very strong very long stems (about 46 to about 72 cm.) for the class. Outdoors the plant blooms freely and nearly continuously during the growing season. The flowers have a very slight tea fragrance.

BUD

The peduncle is of average to long length for the class (about 6 to about 8 cm.), and usually erect. It is moderately smooth with many stipitate glands and some hairs. Peduncle color is between 144A and 138A.

Before the calyx breaks, the bud is of medium size for the class (about 2 to about 3 cm. in diameter at the widest point), moderately long in length (about 3.5 to about 4.5 cm.), and pointed to ovoid in shape. The surface of the bud bears some stipitate glands usually with slender foliaceous parts extending beyond the tip of the bud equal to ½ or more of its length. Bud color is between 144A and 138A.

The inner surface of the sepals is covered with fine wooly tomentum; sepal margins are lined with some stipitate glands and hairs.

As the petals open, the bud is medium to large for the class (about 2.5 to about 3.5 cm. in diameter at the widest point), of moderately long length (about 4 to about 5 cm.), and very pointed to ovoid in form. The predominant color of the under and upper surfaces of the newly opened petals is between 155A and 157D. The edge of the petal is colored with between 61B and 53C which suffuses into the predominant color. The bud does open up well and is not prevented from opening in wet, cold, hot or dry weather.

BLOOM

When fully open, the bloom is of medium to large size for the class, ranging from about 9 to about 12 cm. in diameter. Petalage is double with 28 to 33 petals and 1 to 4 petaloids arranged regularly. When partially open, the bloom form is cupped to high centered and the petals are spiraled with petal edges somewhat rolled outward. When fully open, the bloom form is more cupped and full and the petals are more loosely cupped and undulated with petal edges slightly rolled outward.

PETALS

The petals are of good substance and of medium thickness, with upper and under surfaces slightly satiny. The outer petals are round to broadly obovate in shape with apices very rounded. The inner petals are more narrowly ovate to obovate in shape with apices rounded to flat.

NEWLY OPENED FLOWER

The predominant color of the under and upper surfaces of the outer, intermediate and inner petals is between 155A and 155C. The edge of the petals is colored with between 61C and 54A that suffuses into the predominant color. On the under side of the petals, the edge color suffuses into the predominant color more quickly than on the upper side of the petal.

The general tonality of the newly opened flower is between 155A and 155C with an edging of between 61C and 54A.

THREE DAY OLD FLOWER

The predominant color of the under and upper surface of the outer and inner petals is between 155C and 155D. The edge of the petals is colored with between 66D and 63D which suffuses into the predominant color. On the under side of the petals, the edge color suffuses into the predominant color more quickly than on the upper side of the petal.

The general tonality of the three day old flower is between 155C and 155D with an edging of between 66D and 63D.

On the spent bloom, the petals usually drop off cleanly.

In August, in Upland, Calif., blooms on the bush growing outdoors generally last from four to five or more days. Cut roses grown outdoors and kept at normal indoor living temperatures generally last from five to six or more days.

MALE REPRODUCTIVE ORGANS

Stamens vary in number and are arranged regularly about the pistil. The filaments are of irregular length, most with anthers. The anthers open approximately at the same time. Anther color is near 22B when immature and near 165B at maturity. Pollen is very abundant and near 19C in color.

FEMALE REPRODUCTIVE ORGANS

Pistils are many and vary in number (approximately 110). The styles are uneven and loosely bunched. Stigma color is near 4C. Style color is near 45D. Ovaries are usually all enclosed in the calyx.

Hips are globular in form, and near 21C in color when ripe. The hip surface is very smooth with thick fleshy walls. The sepals fall away soon. Seeds vary in number (approximately 18 to 26).

FOLIAGE

The compound leaves are usually comprised of three to five leaflets and are borne very abundantly. The leaves are very large for the class (about 16 to about 19 cm. in length and about 14 to about 16 cm. in width at the widest point), have leathery texture, and semi-glossy finish. The leaflets are very large for the class (about 6.5 to about 11 cm. in length and about 4 to about 6 cm. in width at the widest point), shaped somewhat oval to ovate with acute apices and round to acute bases. Their margins are usually simply serrate.

The upper surface of the mature leaf is between 147A and 136A. The under surface of the mature leaf is between 138B and 191B. The upper surface of the young leaf is between 147B and 137B, moderately suffused with between 183B and 184B. The under surface of the young leaf is very heavily suffused with between 183B and 184B.

The rachis is moderately heavy in caliper and grooved with few hairs and stipitate glands on the edges of the upper side. The under side of the rachis is very smooth with few hairs and some moderately large prickles of near 160D in coloration.

The stipules are very narrow with short straight points that usually turn out at an angle of more than 90 degrees.

The plant displays an above average degree of resistance to powdery mildew and blackspot as compared to other commercial varieties grown under comparable conditions in Upland, Calif.

GROWTH

The plant has a very upright, very tall habit (about 220 to about 280 cm. in height and about 120 to about 140 cm. in spread at the widest point), with very full branching. It displays very vigorous growth.

The color of the major stems is near 146D. They bear many large prickles which are angled slightly downward; prickle color is near 165B. The major stem bears no small prickles.

The color of the branches is between 144A and 137D. They bear many large prickles which are angled slightly downward; prickle color is between 144C and 160C. The branches bear very few small prickles of similar shape and coloration.

The color of the new shoots is near 144B often lightly suffused with near 183B. They bear many large prickles angled slightly downward; prickle color is near 144C. The shoots bear very few small prickles of similar shape and coloration.

I claim:

1. A new and distinct variety of Hybrid Tea rose substantially as described and illustrated herein.

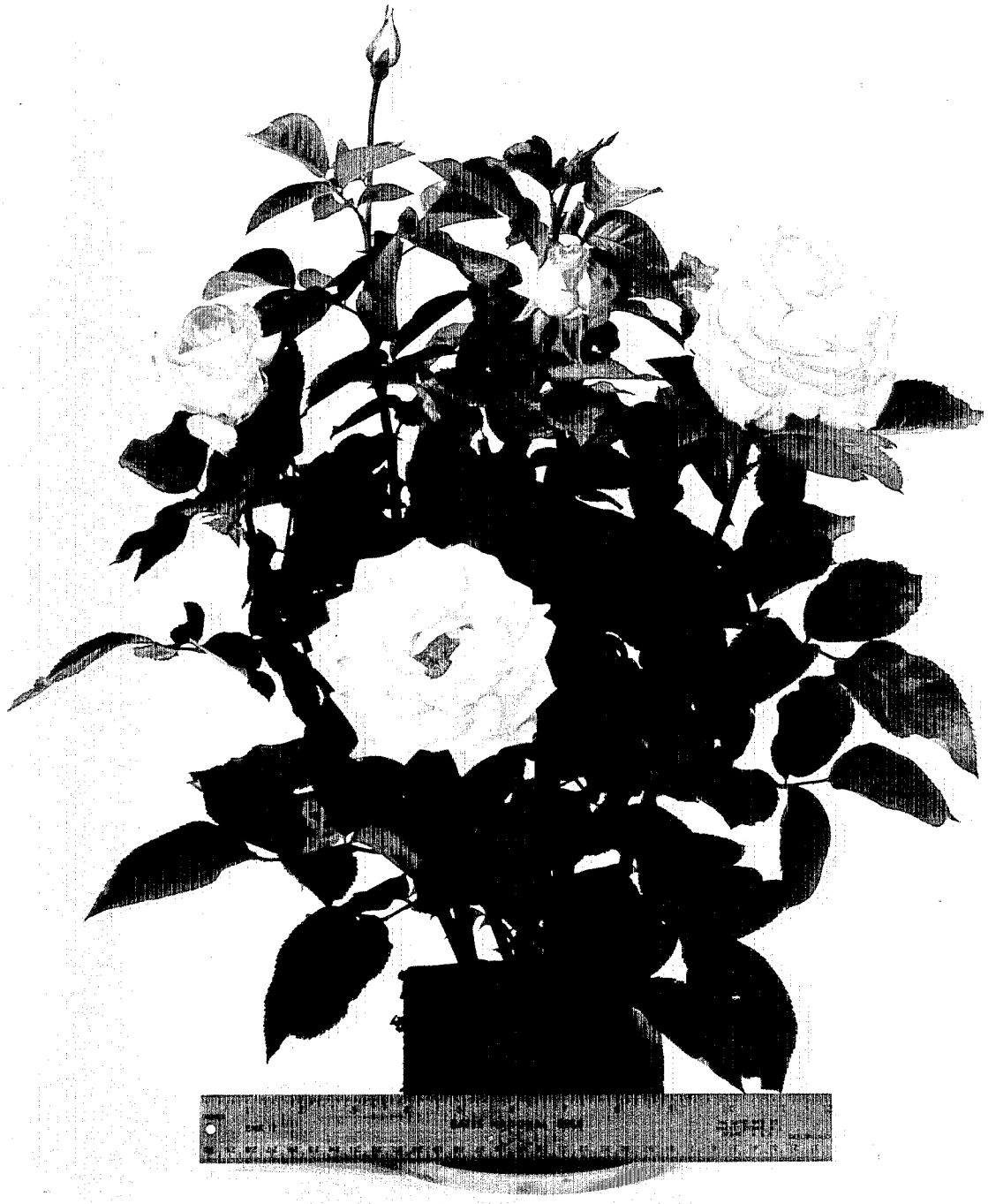

* * * * *